(12) United States Patent
Powers

(10) Patent No.: US 9,386,929 B2
(45) Date of Patent: Jul. 12, 2016

(54) AURAL HEART MONITORING APPARATUS AND METHOD

(75) Inventor: Daniel J. Powers, Issaquah, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 867 days.

(21) Appl. No.: 12/744,954

(22) PCT Filed: Nov. 18, 2008

(86) PCT No.: PCT/IB2008/054840
§ 371 (c)(1),
(2), (4) Date: May 27, 2010

(87) PCT Pub. No.: WO2009/069037
PCT Pub. Date: Jun. 4, 2009

(65) Prior Publication Data
US 2010/0324615 A1    Dec. 23, 2010

Related U.S. Application Data

(60) Provisional application No. 60/990,456, filed on Nov. 27, 2007.

(51) Int. Cl.
A61N 1/39     (2006.01)
A61B 5/024    (2006.01)
A61B 5/00     (2006.01)
A61B 7/04     (2006.01)

(52) U.S. Cl.
CPC ............. *A61B 5/024* (2013.01); *A61B 5/02438* (2013.01); *A61B 5/6815* (2013.01); *A61B 5/6817* (2013.01); *A61B 7/04* (2013.01); *A61N 1/3925* (2013.01); *A61N 1/3987* (2013.01)

(58) Field of Classification Search
CPC ... A61N 1/39; A61N 1/3987; A61N 5/02108; A61N 5/02125
USPC .......................................................... 607/4, 6
See application file for complete search history.

(56) References Cited

U.S. PATENT DOCUMENTS

| 4,549,551 | A | 10/1985 | Dyck et al. |
| 6,004,274 | A | 12/1999 | Nolan et al. |
| 6,253,108 | B1 * | 6/2001 | Rosborough et al. ........... 607/14 |
| 6,283,915 | B1 | 9/2001 | Aceti et al. |
| 6,440,082 | B1 | 8/2002 | Joo et al. |
| 7,135,002 | B2 | 11/2006 | Sullivan |
| 2003/0220584 | A1 * | 11/2003 | Honeyager et al. ........... 600/559 |
| 2003/0233051 | A1 | 12/2003 | Verjus et al. |
| 2005/0043763 | A1 | 2/2005 | Marcovecchio et al. |

(Continued)

FOREIGN PATENT DOCUMENTS

| GB | 2419946 A | 5/2006 |
| JP | 11514898 A | 12/1999 |

(Continued)

*Primary Examiner* — Theodore Stigell
*Assistant Examiner* — Michael D Abreu

(57) ABSTRACT

A heart monitor is disclosed including an electroacoustic transducer such as an earphone coupled to a controller. The transducer is positioned in a person's ear in acoustic communication with the tympanum. Signals from the transducer are processed to determine the presence of pulsatile blood flow. The heart monitor may be incorporated into a defibrillator to sense the presence of blood flow for use in a shock delivery decision.

4 Claims, 7 Drawing Sheets

(56) References Cited

U.S. PATENT DOCUMENTS

2006/0064037 A1 3/2006 Shalon et al.
2014/0155787 A1 6/2014 Freeman et al.

FOREIGN PATENT DOCUMENTS

| JP | 2012075936 A | 4/2012 |
| WO | 2007004083 A1 | 1/2007 |

* cited by examiner

AURAL HEART MONITORING APPARATUS AND METHOD

This invention relates generally to systems and methods for measuring heart activity and, more particularly, to sensing pulsatile blood flow using an electroacoustic transducer positioned proximate to the ear which detects pulse and provides audio output.

Personal digital assistants (PDAs), portable digital music players, cell phones, and other electronic devices have become ubiquitous. Portable digital music players are particularly popular as they can store a user's entire library of music and can be taken anywhere. They are particularly well suited for use while jogging such as they are not affected by movement. Recently, products have emerged that enable a portable digital music player to function as a pedometer, measuring a person's footsteps to provide an estimate of speed and distance traveled. Based on this information some products further provide an estimate of calories burned.

Although these functions are helpful they do not provide a complete picture of a person's workout. The more critical aspect of exercise is maintaining one's heart rate at a level high enough to provide a good workout without causing injury or premature burnout. Experts suggest that maintaining the heart rate between 50 and 85 percent of a one's maximum heart rate enables one to maximize the benefits of a workout while avoiding injury.

In view of the foregoing it would be advantageous to incorporate into a portable digital music player a means for measuring and displaying a person's heart rate.

In accordance with the principles of the present invention, a portable media playback device includes an electroacoustic transducer mounted to an ear piece adapted to be positioned within a user's ear. A receiving circuit and a controller are coupled to the transducer. The controller is programmed to selectively read media files form a media storage device and convert them to signals coupled to the transducer. The controller is further programmed to receive signals from the transducer and process the signals to determine the user's heart rate.

In another aspect of the invention a signal conditioning circuit receives the signals from the transducer and filters them to remove noise. The signal conditioning circuit may also perform common mode noise reduction using the signals from a pair of transducers.

In another aspect of the invention, the controller receives signals from one transducer while outputting signals to another transducer.

In another embodiment of the present invention, a heart monitoring system is incorporated into an automatic external defibrillator. The heart monitoring system receives signals from an electroacoustic transducer, such as an earphone mounted within an ear piece, and processes the signals to determine the presence of pulsatile blood flow in a subject. This arrangement is useful for confirming an ECG analysis that indicates a shock is needed by the absence of sensed pulsatile activity from the patient's ear canal. Correspondingly, a sensed pulsatile activity in the patient's ear contraindicates the need for a resuscitation shock. The arrangement is especially useful in a "pulseless electrical activity" (PEA) situation, where the lack of a sensed pulse in the ear canal will contradict an ECG analysis that indicates the presence of effective electrical activity in the heart.

Figure 1:
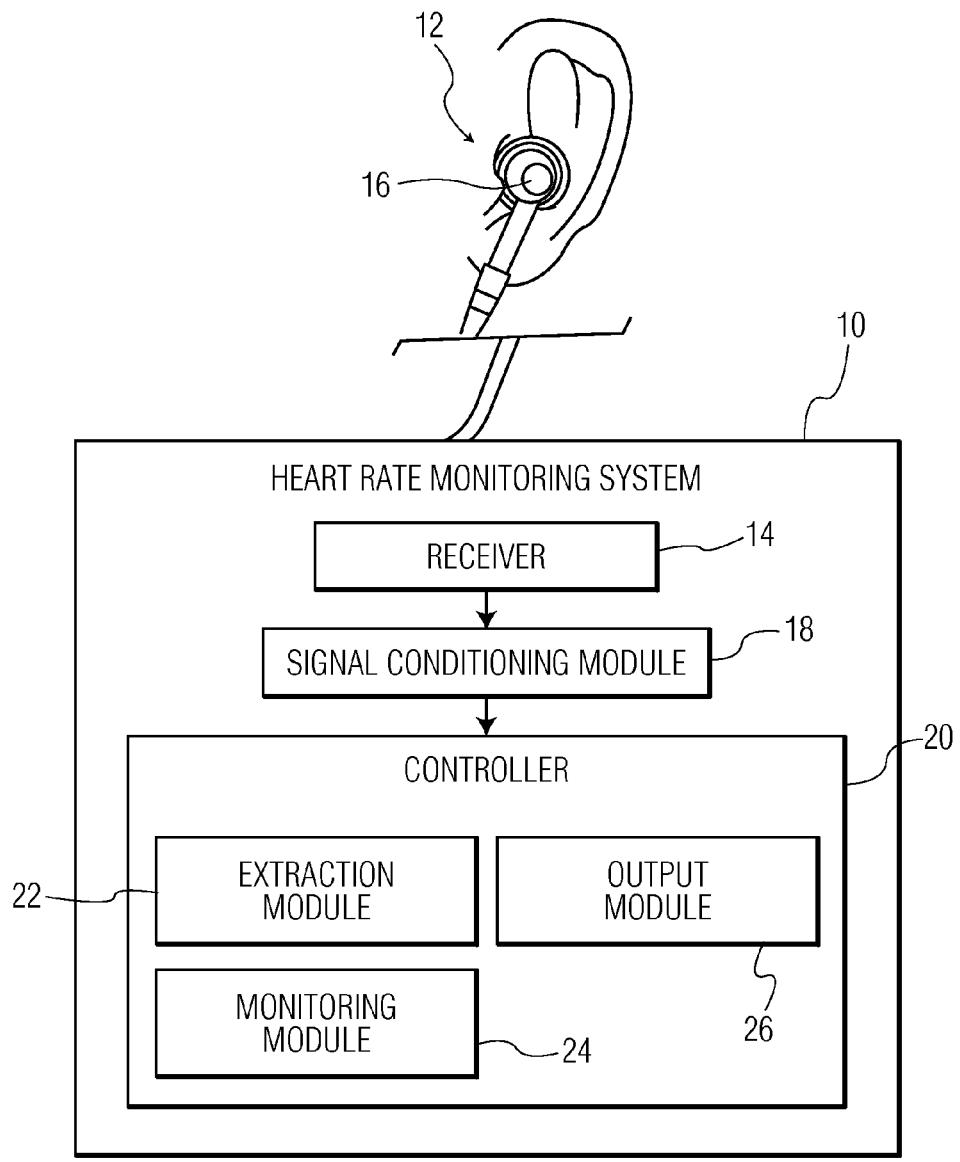
FIG. 1 is a schematic block diagram of a system for measuring a person's heart rate in accordance with an embodiment of the present invention.

Referring to FIG. 1, a heart monitoring system 10 includes an electroacoustic transducer 12, such as an audio earphone, coupled to a receiver 14. The transducer 12 is mounted within an ear piece 16 that is adapted to mount to a user's ear. The ear piece 16 may be positioned around the user's auricle, nested in the user's auricle, or inserted in the user's ear canal.

The receiver 14 receives signals from the transducer 12 and outputs them to a signal conditioning module 18. The signal conditioning module 18 amplifies and removes noise from the signal. In some embodiments, the signal conditioning module 18 performs low pass filtering on the signal to remove frequency content that is the result of noise. In some embodiments, two transducers 12 are used, one for each of the user's ears. In such embodiments, the signal conditioning module 18 may use signals from both transducers to perform common mode noise rejection.

The output of the signal conditioning module 18 is provided to a controller 20 including an extraction module 22, a monitoring module 24, and an output module 26. In some embodiments, the signal conditioning module 18 is also incorporated into the controller 20.

Figure 2:
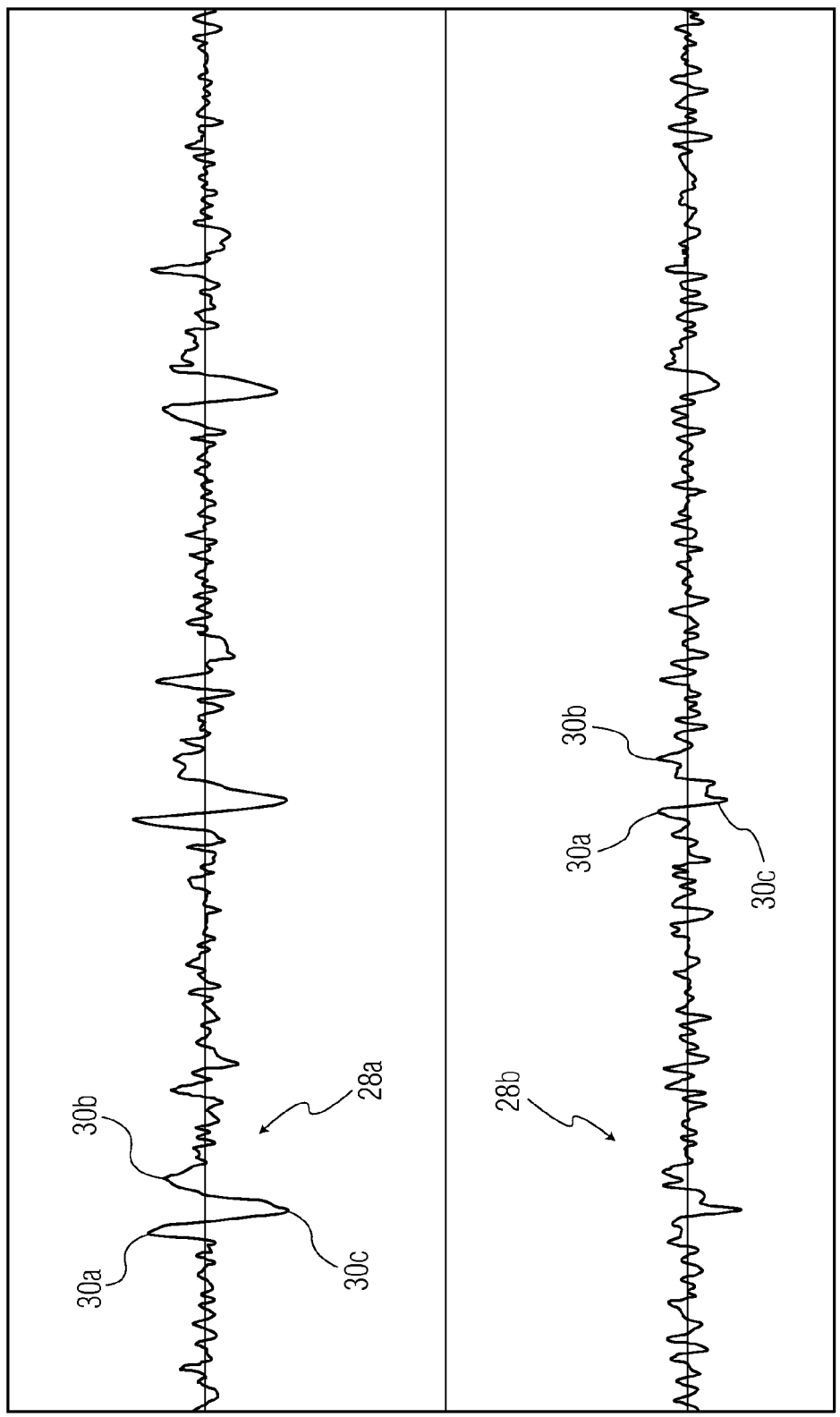
FIG. 2 is a graph plotting the output of an electroacoustic transducer conditioned to facilitate extraction of a person's heart rate.

Referring also to FIG. 2, the extraction module 22 analyzes the conditioned signal in order to isolate individual heart beats. As shown in the plots 28a, 28b, which represent signals detected in a user's two ears, portions of the received pulsatile signals correspond to a person's heart beat including portions 30a, 30b corresponding to the $S_1$ and $S_2$ tones, respectively, of the heart beat. Also apparent is a low pressure portion 30c occurring between the $S_1$ and $S_2$ tones. As is apparent in FIG. 2, the heart beat may be readily identified in one ear or the other. Accordingly, the extraction module 22 may use one, both, or a weighted combination, of the received signals in order to determine the user's pulsatile blood flow and, if desired, measurements thereof such as heart rate. The extraction module 22 may, for example, evaluate the quality of the signal from each ear and use only the one having the highest quality to isolate the heart rate. Quality may be determined by evaluating and comparing the signal-to-noise ratio of the signals as known in the art. In other embodiments the signals from the two ears may be correlated to identify the heart beat signal.

The extraction module 22 may extract the heart beats from the signal from the transducer 12, or signals from two transducers 12, by locating the $S_1$ and $S_2$ tones. As is apparent in plot 28b, the low pressure portion 30c between the $S_1$ and $S_2$ tones 30a, 30b is of relatively large magnitude even though the $S_1$ and $S_2$ tones are of relatively weak magnitude. Accordingly, the extraction module 22 may identify heart beats by identifying the low pressure portion 30c in place of or in addition to locating the $S_1$ and $S_2$ tones 30a, 30b. In some embodiments, the extraction module 22 identifies individual heart beats by using conventional methods, such as those disclosed in U.S. Pat. Nos. 4,549,551 and 7,135,002.

The monitoring module 24 evaluates the timing of the beats to determine the user's heart rate. The monitoring module 24 may record the heart rate over time and produce values derived from the recorded data, such as average heart rate, minimum and maximum heart rate, amount of time the heart rate falls within a target range of heart rates. For example, a user may input into the monitoring module a range of heart rates within which the user's heart rate should remain during a workout to improve results and avoid injury. In some embodiment, a user may input a maximum heart rate and the monitoring module will calculate a range of heart rates in which the user's heart rate should remain to improve results. In some embodiments, the monitoring module 24 produces a plot showing variation in heart rate over time.

The output module 26 outputs the heart rate and values derived from the heart rate to the user. The output module 26 may output the data to a display device (not shown) coupled to the controller 20, such as an LCD or other digital display. In embodiments where the transducer 12, or transducers 12, are embodied as audio earphone, the output module 26 may generate a audio message that is output through the earphone. In other embodiments, the output module 26 produces a wireless signal that is received by another device having a receiver and a display, and used to generate an output for display to a user.

Figure 3:
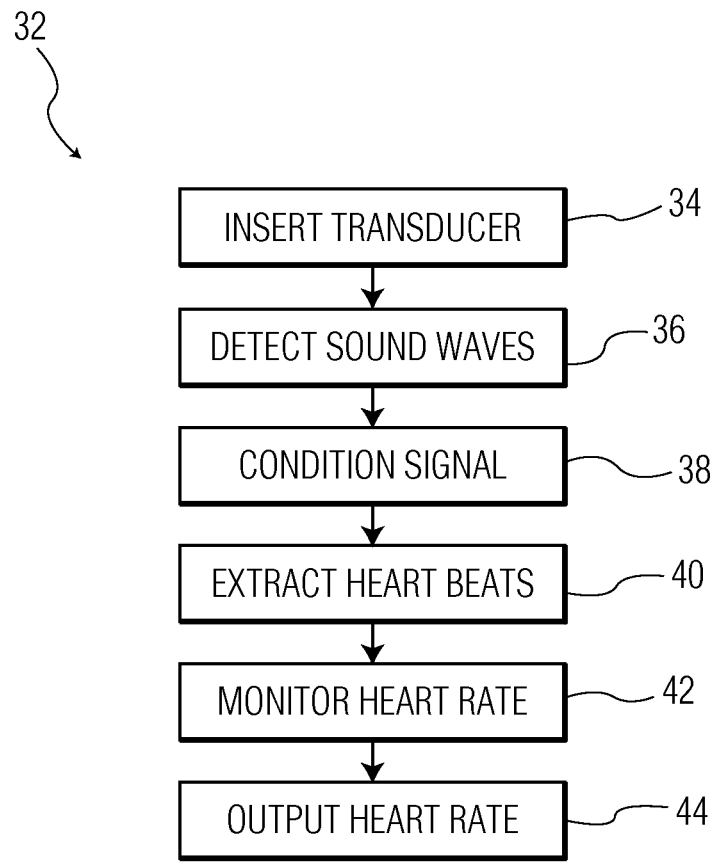
FIG. 3 is a flow diagram for measuring a person's heart rate in accordance with an embodiment of the present invention.

Referring to FIG. 3, a method 32 for measuring a heart rate includes inserting an electroacoustic transducer into a person's ear at step 34. Step 34 may include positioning the transducer around the person's ear or into the person's auricle or ear canal. At step 36, sound waves induced in the person's tympanum by blood flow therethrough are communicated to the transducer and converted into electrical signals by the transducer. At step 38, the electrical signals are conditioned to remove noise. Step 38 may include one or both of low pass filtering and common mode noise rejection using the output of two transducers placed in two ears. At step 40, the conditioned signal is processed to extract a person's heart beats and at step 42 the beats are monitored to calculate a heart rate. Other values related to the heart rate over time can be calculated as well, such as average, maximum, and minimum heart rate during a monitoring period or the duration of time in which the heart rate has been within a target range. At step 44, an output is produced indicating the user's heart rate and/or the values corresponding to the heart rate over time. Producing an output 44 may include producing a visual display or an audible verbal message presented over the same transducer used to detect the person's heart rate.

Figure 4:
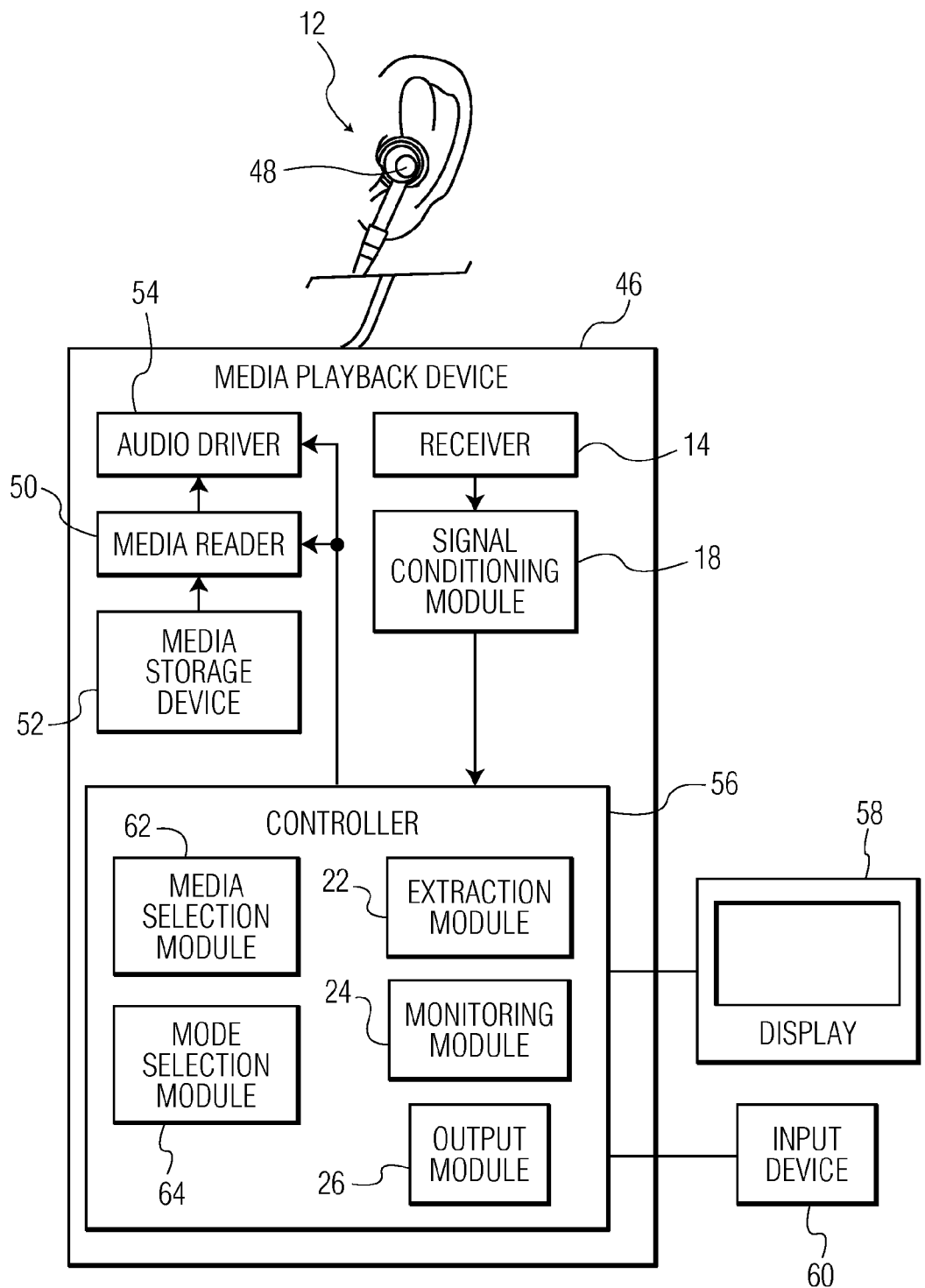
FIG. 4 is a schematic block diagram of a media playback device including a system for measuring a person's heart rate in accordance with an embodiment of the present invention.

Referring to FIG. 4, a heart rate monitoring system is incorporated into a portable media playback device 46. In such embodiments, the electroacoustic transducers 12 may be embodied as earphone 48, such as the illustrated earphone adapted to be inserted within the auricle of a user, or as any other type of earphone known in the art. The device 46 includes a media reader 50 for reading media data from a media storage device 52, such as a flash memory, hard drive, compact disc, audio tape, or the like. The media data from the media reader 50 is provided to an audio driver 54 that converts the media data into electrical signals that are coupled to the earphone 48 to produce sound.

The media reader 50 and audio driver 54 are controlled by a controller 56 incorporating an extraction module 22, monitoring module 24, and output module 26 of the heart rate monitoring system. The earphone 48 may also be coupled to the controller 56 by a receiver 14 and signal conditioning module 18.

The controller 56 may be coupled to a display 58, such as an LCD or other display device, for presenting information to a user. The controller 56 may include a media selection module 62 that receives one or more inputs from one or more input devices 60 such as a touch pad and/or one or more buttons. The media selection module 62 receives the inputs and selects a media file from the media storage device 52 for playback based on the inputs.

The controller 56 may further include a mode selection module 64. The mode selection module 64 selects whether the media playback device 46 is to function as a media playback device or as a heart monitor. In some embodiments, the mode selection module 64 selects which of the earphones 48 is to output audio signals and which is to receive signals for monitoring a user's heart rate. For example, the mode selection module 64 may cause one earphone to output music while the other earphone is simultaneously measuring the user's heart rate.

In other embodiments, the mode selection module 64 measures the user's heart rate between playback of media files. For example, the mode selection module 64 may switch the mode from playback to heart rate monitoring for a brief period, such as two to five seconds after a song, during which period the user's heart rate is monitored by receiving signals at the receiver and processing them as discussed above. The mode selection module 64 may then cause the media reader 50 and audio driver 54 to output another song to the earphone 48.

Figure 5:
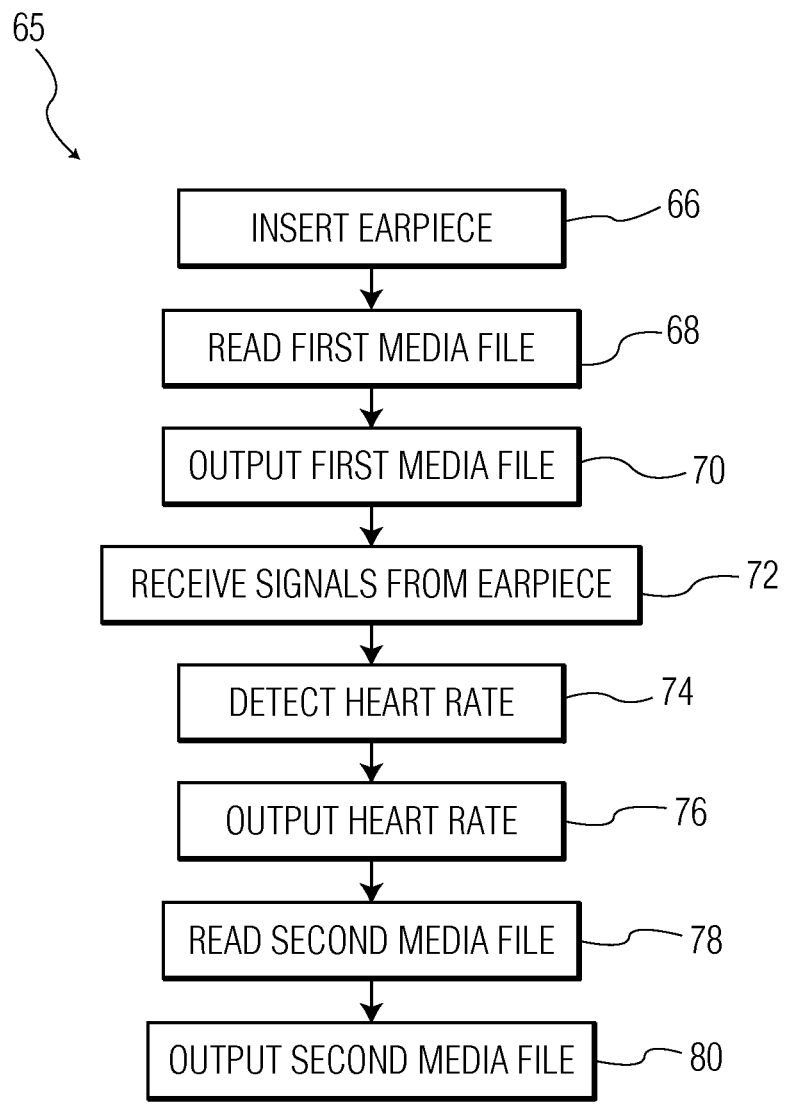
FIG. 5 is a flow diagram of a method for incorporating heart rate monitoring into media playback in accordance with an embodiment of the present invention.

Referring to FIG. 5, a method 65 for combining media playback with heart rate monitoring may include inserting an earpiece in a user's ear, either in the auricle or ear canal, at step 66. The method 64 further includes reading a first media file from a media storage device at step 68 and outputting the media file to an earpiece at step 70. At step 72, signals from the earpiece are received following output of the media file at step 70. At step 74 the received signals are processed to extract the user's heart rate. At step 76 the heart rate is output, such as by means of a display or verbal message output over the earpiece. At step 78, following receiving signals from the earpiece at step 72, a second media file is read from the media storage device and at step 80 the second media file is output to the earpiece.

Figure 6:
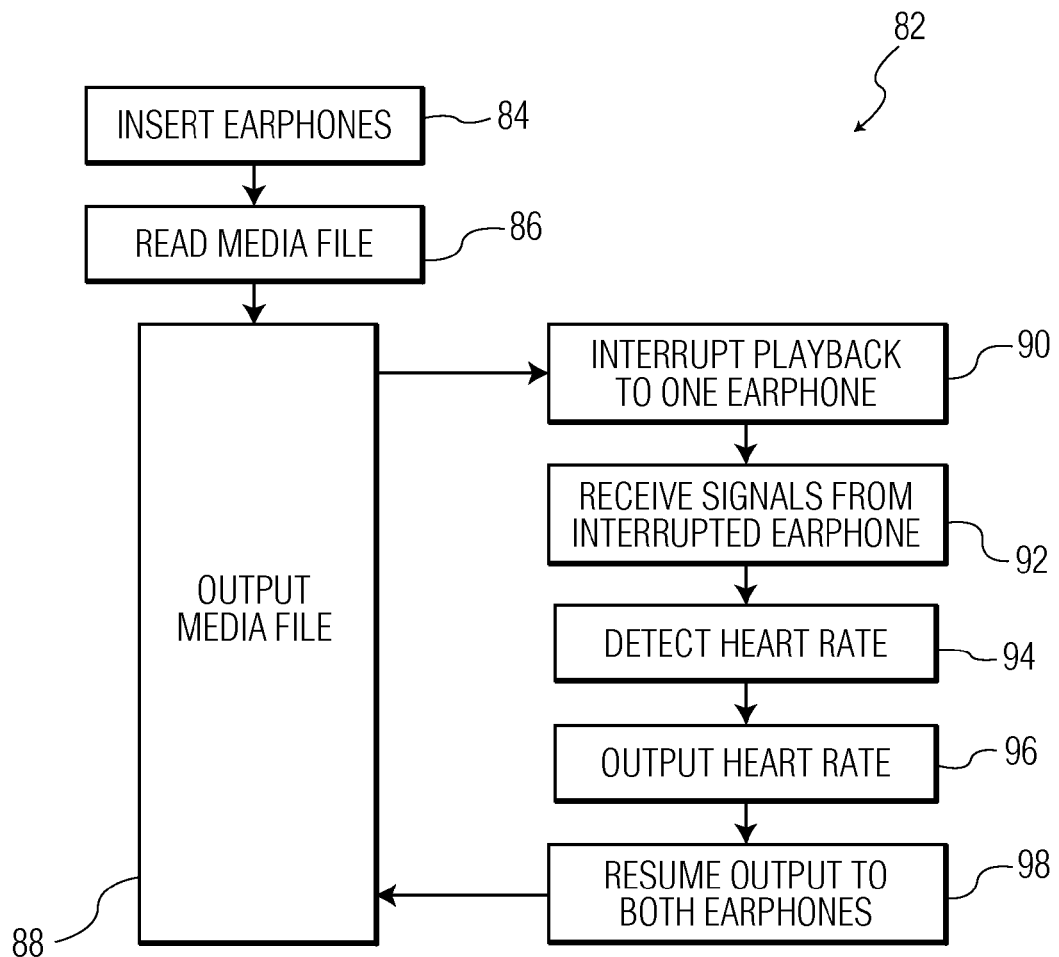
FIG. 6 is a flow diagram of an alternative method for incorporating heart rate monitoring into media playback in accordance with an embodiment of the present invention.

Referring to FIG. 6, a method 82 is performed. Method 82 includes inserting two earphones in a user's ears, either in the auricles or ear canals, at step 84. The method 82 further includes reading a media file from a media storage device at step 86 and outputting the media file to the earphones at step 88. Output to one of the earphones is interrupted at step 90 while continuing playback on the other earphone. Signals are received from the interrupted earphone at step 92. At step 94, the received signals are processed to extract the user's heart rate. At step 96 the heart rate is output, such as by means of a display or verbal message output over the earphone. In some embodiments, the output is delayed until requested by a user, such as in response to an input. In such embodiments, step 96 may be replaced with storing the heart rate for later presentation. At step 98, the media file is again output to both earphones.

In some embodiments, the method 82 is repeated with playback to the other earphone being interrupted. at step 90. The method 82 may further include comparing the signals received from each ear during step 92 to determine which ear provides a better signals to noise ratio. Following this comparison, in subsequent iterations of the method 82, only the ear found to have the higher signal to noise ratio is interrupted at step 90.

Figure 7:
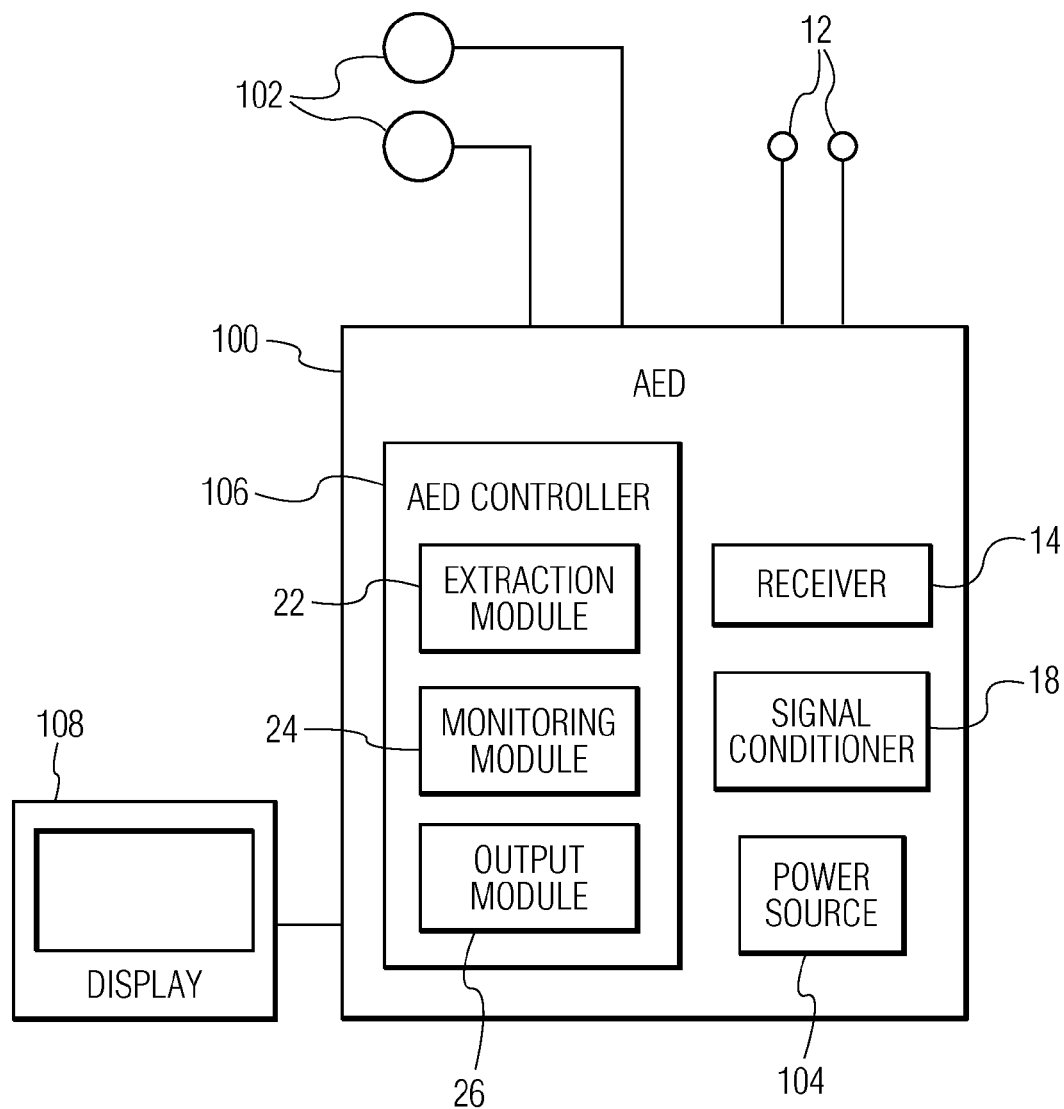
FIG. 7 is a schematic block diagram of an automatic external defibrillator (AED) incorporating a system for indicating the presence of pulsatile blood flow in accordance with an embodiment of the present invention.

Referring to FIG. 7, a blood flow monitoring system 10 is incorporated into an automatic external defibrillator (AED) 100. The AED includes electrodes 102 for contacting a victim's skin when administering a shock. The AED 100 further includes a power source 104 providing electrical power for delivering a shock. The AED 100 further includes a controller 106 that is programmed to control the delivery of electrical power from the power source 102 to the electrodes 100. The controller 106 also detects the electrical activity of the victim's heart through the electrodes 102 and analyzes the electrical activity to determine whether a shock should be administered.

In the illustrated embodiment, the controller 106 further includes the extraction module 22, monitoring module 24, and output module 26 as discussed above for monitoring a patient's pulsatile blood flow using electroacoustic transducers 12, such as headphones or earphones. The AED 100 likewise includes a receiver 14 and signal conditioner 18 for receiving signals from the transducers 12. In some embodiments, the AED 100 includes a display 108 and the controller is programmed to display instructions for operating the AED on the display 106. In such embodiments, the output module 26 of the heart monitoring system may determine that the patient is presenting pulsatile blood flow from the detection of acoustic signals in the ear canal as discussed above and output to the display 108 an indication of the blood flow condition and other values determined by monitoring the pulsatile signals, when present, over time. In other embodiments the blood flow indication signal is output as an audible signal.

From the foregoing it will be appreciated that, although specific embodiments of the invention have been described herein for purposes of illustration, various modifications may be made without deviating from the spirit and scope of the invention. Reference to modules and other elements constituting embodiments of the invention indicate structures and steps for performing the functions attributed to a module, however the structures for performing the functions attributed to a module or other element may be operate at different times or include multiple distinct structures that may or may not be collocated. Accordingly, the invention is not limited except as by the appended claims.

What is claimed is:

1. An automatic external defibrillator (AED) comprising:
    a pair of electrodes adapted to contact a subject;
    an ECG processor, coupled to the electrodes, which acts to analyze an ECG signal;
    an energy source;
    a high voltage circuit coupled to the energy source;
    a shock delivery circuit coupled to the ECG processor, the high voltage circuit, and the electrodes;
    an earphone adapted to detect acoustic signals of the ear of the subject; and
    an earphone signal processor, coupled to the earphone, which operates to sense the presence of pulsatile blood flow from signals received by the earphone,
    wherein the signal processor is coupled to the shock delivery circuit,
    wherein the shock delivery circuit makes a decision to shock based upon an absence of a pulsatile ECG signal from the ECG processor and an absence of pulsatile blood flow sensed by the earphone signal processor.

2. The automatic external defibrillator of claim 1, wherein the earphone signal processor further comprises a signal conditioning circuit responsive to signals produced by the earphone.

3. The automatic external defibrillator of claim 1, wherein the shock delivery circuit contraindicates a decision to shock in the presence of pulsatile blood flow sensed by the earphone signal processor.

4. The automatic external defibrillator of claim 1, wherein a condition of pulseless electrical activity is indicated by the detection of a pulsatile ECG signal by the ECG processor and the absence of pulsatile blood flow as sensed by the earphone.

* * * * *